United States Patent
Yamamoto et al.

(10) Patent No.: US 12,201,602 B2
(45) Date of Patent: *Jan. 21, 2025

(54) MEDICAMENT COMPRISING COMBINATION OF SEPETAPROST AND Rho-associated COILED-COIL CONTAINING PROTEIN KINASE INHIBITOR

(71) Applicant: SANTEN PHARMACEUTICAL CO., LTD., Osaka (JP)

(72) Inventors: Yasuko Yamamoto, Ikoma (JP); Takazumi Taniguchi, Ikoma (JP)

(73) Assignee: SANTEN PHARMACEUTICAL CO., LTD., Osaka (JP)

( * ) Notice: Subject to any disclaimer, the term of this patent is extended or adjusted under 35 U.S.C. 154(b) by 159 days.

This patent is subject to a terminal disclaimer.

(21) Appl. No.: 17/887,854

(22) Filed: Aug. 15, 2022

(65) Prior Publication Data

US 2022/0387372 A1    Dec. 8, 2022

Related U.S. Application Data

(63) Continuation of application No. 16/955,857, filed as application No. PCT/JP2018/046970 on Dec. 20, 2018, now Pat. No. 11,446,273.

(30) Foreign Application Priority Data

Dec. 21, 2017  (JP) ................. 2017-244847
Sep. 26, 2018  (JP) ................. 2018-180658

(51) Int. Cl.
  *A61K 31/335*   (2006.01)
  *A61K 31/472*   (2006.01)
  *A61K 31/551*   (2006.01)
  *A61P 27/06*    (2006.01)

(52) U.S. Cl.
  CPC .......... *A61K 31/335* (2013.01); *A61K 31/472* (2013.01); *A61K 31/551* (2013.01); *A61P 27/06* (2018.01)

(58) Field of Classification Search
  CPC .................................................. A61K 31/335
  See application file for complete search history.

(56) References Cited

U.S. PATENT DOCUMENTS

| | | | |
|---|---|---|---|
| 4,952,581 A | 8/1990 | Bito et al. | |
| 7,972,612 B2 | 7/2011 | Hatano et al. | |
| 8,048,888 B2* | 11/2011 | Wosikowski-Buters | A61K 31/555 514/266.4 |
| 8,455,477 B2* | 6/2013 | Katz | A61P 3/10 514/210.18 |
| 8,614,340 B2* | 12/2013 | Kambe | C07D 401/06 549/355 |
| 8,685,986 B2 | 4/2014 | Hagihara et al. | |
| 8,962,868 B2 | 2/2015 | Kambe et al. | |
| 9,388,157 B2 | 7/2016 | Kambe et al. | |
| 9,889,114 B2 | 2/2018 | Kambe et al. | |
| 10,201,520 B2 | 2/2019 | Kambe et al. | |
| 2003/0018079 A1 | 1/2003 | Richardson et al. | |
| 2005/0245509 A1 | 11/2005 | Nakajima et al. | |
| 2006/0052367 A1 | 3/2006 | Hatano et al. | |
| 2010/0041671 A1 | 2/2010 | Nakajima et al. | |
| 2010/0063060 A1 | 3/2010 | Nakajima et al. | |
| 2011/0263638 A1 | 10/2011 | Hatano et al. | |
| 2012/0040994 A1 | 2/2012 | Nakajima et al. | |
| 2012/0122964 A1 | 5/2012 | Kambe et al. | |
| 2012/0190852 A1 | 7/2012 | Hagihara et al. | |
| 2013/0310370 A1* | 11/2013 | Mizuno | A61P 27/02 514/218 |
| 2013/0324577 A1 | 12/2013 | Kambe et al. | |
| 2014/0073676 A1 | 3/2014 | Kambe et al. | |
| 2015/0112079 A1 | 4/2015 | Kambe et al. | |
| 2016/0287551 A1 | 10/2016 | Kambe et al. | |
| 2018/0116995 A1 | 5/2018 | Kambe et al. | |
| 2019/0111019 A1 | 4/2019 | Kambe et al. | |
| 2020/0093781 A1 | 3/2020 | Kambe et al. | |
| 2020/0316009 A1 | 10/2020 | Yamamoto et al. | |

FOREIGN PATENT DOCUMENTS

| | | |
|---|---|---|
| EP | 2671586 A1 | 12/2013 |
| JP | 2726672 B2 | 3/1998 |
| JP | 2004107335 A | 4/2004 |
| WO | 0238158 A1 | 5/2002 |
| WO | 2004019951 A1 | 3/2004 |

(Continued)

OTHER PUBLICATIONS

Bartlett "Exploiting Chemical Diversity for Drug Discovery" Edited by Paul A Bartlett and Michael Entzeroth, The Royal Society of Chemistry, 2006, pp. 113-118.*
"Find ETDs Home >> Thesis Resources >> Find ETDs" Online: "https://ndltd.org/thesis-resources/find-etds/" Accessed Jan. 31, 2023.*
Irwin "ZINC—A Free Database of Commercially Available Compounds for Virtual Screening" J. Chem. Inf. Model. 2005, 45, 177-182.*
Kim "PubChem in 2021: new data content and improved web interfaces" Nucleic Acids Research, 2021, vol. 49, Database issue Published online Nov. 5, 2020.*
STN Registry/Zregistry (CAS Registrysm) Sep. 2016 2 pages.*
Jones, Drugs (2014) 74:2211-2215.*
Sturdivant, Bioorg. Med. Chem. Lett. 26 (2016) 2475-2480.*

(Continued)

*Primary Examiner* — Nizal S Chandrakumar
(74) *Attorney, Agent, or Firm* — BUCHANAN, INGERSOLL & ROONEY PC

(57) ABSTRACT

Described is a combination of a prophylactic or therapeutic agent for glaucoma or ocular hypertension, which is useful as a prophylactic or therapeutic agent for glaucoma or ocular hypertension. By combining sepetaprost and a Rho-associated coiled-coil containing protein kinase inhibitor(s), an intraocular pressure lowering action is enhanced as compared with the case where each drug is used alone. As the form of administration, they may be administered concomitantly or may be administered as a combination drug.

11 Claims, 1 Drawing Sheet

(56) References Cited

FOREIGN PATENT DOCUMENTS

| WO | 2004045644 A1 | 6/2004 |
|---|---|---|
| WO | 2010113957 A1 | 10/2010 |
| WO | 2011013651 A1 | 2/2011 |
| WO | 2012102357 A1 | 8/2012 |
| WO | 2012105674 A1 | 8/2012 |

OTHER PUBLICATIONS

Lewis, Richard A., et al., "Fixed-dose combination of AR-13324 and latanoprost: a double-masked, 28-day, randomised, controlled study in patents with open-angle glaucoma or ocular hypertension", Br. J. Ophthalmol., 2016, vol. 100, pp. 339-344.
Extended European Search Report issued Jul. 26, 2021, by the European Patent Office in corresponding European patent application No. 18891292.7. (14 pages).
International Search Report (PCT/ISA/210) mailed on Mar. 26, 2019, by the Japanese Patent Office as the International Searching Authority for International Application No. PCT/JP2018/046970.
Lu, I. J. et al., "Novel Pharmacologic Candidates for Treatment of Primary Open-Angle Glaucoma", The Yale Journal of Biology and Medcine, vol. 90, No. 1, Mar. 1, 2017, pp. 111-118.
Written Opinion (PCT/ISA/237) mailed on Mar. 26, 2019, by the Japanese Patent Office as the International Searching Authority for International Application No. PCT/JP2018/046970.
Yamagishi, Reiko, et al., "01-045 Action of a new FP/EP3 dual agonist sepetraprost on mouse intraocular pressure", Journal of Japanese Ophthalmological Society, Mar. 2017, vol. 121, p. 183 special extra edition, and English translation thereof.
Dubiner, Harvey, et al., "Fixed dose combination of AR-13324 and latanoprost (PG324): A double-masked, randomized, controlled study in patients with open-angle glaucoma (OAG) or ocular hypertension (OHT)", Invest. Ophthalmol. Vis. Sci., vol. 56, 2015. (2 pages).
Ellis, Eydie Miller, et al., "Ocular hypotensive effect of the novel EP3/FP agonist ONO-9054 versus Xalatan: results of a 28-day, double-masked, randomised study", Br. J. Ophthalmol., 2016, vol. 101, pp. 796-800.
Higginbotham, "Considerations in glaucoma therapy: fixed combinations versus their component medications", Clinical Ophthalmology, 2010, 4, pp. 1-9.
Jones, "Ripasudil: First Global Approval", Drugs, vol. 74, 2014, pp. 2211-2215.
Yamagishi, Reiko, et al., "IOP Lowing Effect of Sepetaprost on Mouse Eye", World Glaucoma Congress, 7th, Jun. 2017, p. 534.
Tanihara, Hidenobu, et al., "One-year clinical evaluation of 0.4% ripasudil (K-115) in patients with open-angle glaucoma and ocular hypertension", Acta Ophthalmologica, 2016, vol. 94, e26-e34.
Germano et al., "Rho kinase inhibitors for glaucoma treatment—Review", Arq Bras Oftalmol, 2015; 78(6), pp. 388-391.
Harris et al., "Ocular Hypotensive Effect of ONO-9054, an EP3/FP Receptor Agonist: Results of a Randomized, Placebocontrolled, Dose Escalation Study", J Glaucoma, vol. 25, No. 10, Oct. 2016, pp. e826-e833.

* cited by examiner

MEDICAMENT COMPRISING COMBINATION OF SEPETAPROST AND Rho-associated COILED-COIL CONTAINING PROTEIN KINASE INHIBITOR

CROSS-REFERENCE TO RELATED APPLICATIONS

The present application is a continuation of U.S. patent application Ser. No. 16/955,857, filed on Jun. 19, 2020, which is a national stage application of PCT/JP2018/046970, filed on Dec. 20, 2018, and which claims priority to Japanese Patent Application No. 2017-244847, filed on Dec. 21, 2017, and Japanese Patent Application No. 2018-180658, filed on Sep. 26, 2018, the entire contents of all of which are hereby incorporated by reference.

TECHNICAL FIELD

The present invention relates to a prophylactic or therapeutic agent for glaucoma or ocular hypertension, which is characterized in that sepetaprost and a Rho-associated coiled-coil containing protein kinase inhibitor(s) are administered in combination. The present invention also relates to a prophylactic or therapeutic agent for glaucoma or ocular hypertension comprising sepetaprost, which is characterized by being used concomitantly with a Rho-associated coiled-coil containing protein kinase inhibitor(s).

BACKGROUND ART

Glaucoma is a refractory eye disease caused by suffering from damage of the internal tissue (retina, optic nerve, etc.) of the eyeball due to the intraocular pressure increases resulted from various pathogenesis. As a method for treating glaucoma, intraocular pressure lowering therapy is generally used, and typical examples thereof include drug therapy, laser therapy, surgical therapy, etc.

In the drug therapy, drugs such as sympathomimetics (non-selective stimulants such as dipivefrin, etc., and $\alpha_2$ receptor agonists such as brimonidine, etc.), sympathetic nerve blockers (β receptor blockers such as timolol, befunolol, carteolol, nipradilol, betaxolol, levobunolol, metipranolol, etc., and $\alpha_1$ receptor blockers such as bunazosin hydrochloride, etc.), parasympathomimetics (pilocarpine, etc.), carbonic anhydrase inhibitors (acetazolamide, etc.), prostaglandins (isopropyl unoprostone, latanoprost, travoprost, bimatoprost, etc.), and Rho-associated coiled-coil containing protein kinase inhibitors (ripasudil), etc., have been used.

Also, in order to obtain a more potent effect of lowering an intraocular pressure, some reports have been made that drugs having an intraocular pressure lowering effect are used in combination. For example, in JP Patent No. 2,726,672 (Patent Document 2), administration of a combination of a sympathetic nerve blocker and a prostaglandin has been reported. Also, in WO 2002/38158 (Patent Document 3), a therapeutic method for glaucoma by administering several drugs having an intraocular pressure lowering action in combination to the eye has been disclosed. Further, in WO 2004/019951 (Patent Document 4), administration of a combination of a Rho-associated coiled-coil containing protein kinase inhibitor and a prostaglandin has been reported, and in WO 2004/045644 (Patent Document 5), combination administration of a Rho-associated coiled-coil containing protein kinase inhibitor and a β receptor blocker has been reported. In addition, a combination drug of dorzolamide and timolol, a combination drug of latanoprost and timolol, a combination drug of brimonidine and timolol and the like are commercially available (Non-Patent Document 1).

By the way, sepetaprost is the compound represented by the formula (1):

[Formula 1]

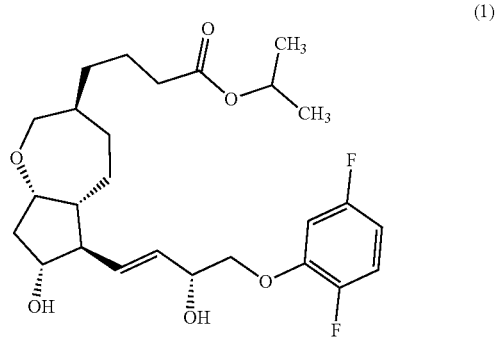

and described in Patent Document 6 as one of the huge number of the compounds. Since these compounds have a potent and sustained intraocular pressure lowering action, there are described that they are expected to be a therapeutic agent for glaucoma.

PRIOR ART DOCUMENTS

Patent Documents

Patent Document 1: WO 2010/113957
Patent Document 2: JP Patent No. 2,726,672
Patent Document 3: WO 2002/38158
Patent Document 4: WO 2004/019951
Patent Document 5: WO 2004/045644
Patent Document 6: WO 2011/013651

Non-Patent Documents

Non-Patent Document 1: Clinical Ophthalmology, 2010, 4, 1-9

SUMMARY OF THE INVENTION

Problems to be Solved by the Invention

It is a very interesting task to find out a combination of prophylactic or therapeutic agents for glaucoma or ocular hypertension, which is useful as a prophylactic or therapeutic agent for glaucoma or ocular hypertension.

Means for Solving the Problems

The present inventors have intensively studied the effect of the combination of prophylactic or therapeutic agents for glaucoma or ocular hypertension, and as a result, they have found that by using sepetaprost and a Rho-associated coiled-coil containing protein kinase inhibitor(s) in combination, an intraocular pressure lowering action is enhanced as compared with the case where each drug is used alone, whereby they have accomplished the present invention.

That is, the present invention relates to the following.

(1) A prophylactic or therapeutic agent for glaucoma or ocular hypertension which is characterized in that sepetaprost and a Rho-associated coiled-coil containing protein kinase inhibitor(s) are administered in combination.
(2) The prophylactic or therapeutic agent described in the above-mentioned (1), which is a combination drug comprising sepetaprost and the Rho-associated coiled-coil containing protein kinase inhibitor(s).
(3) The prophylactic or therapeutic agent described in the above-mentioned (1), wherein sepetaprost and the Rho-associated coiled-coil containing protein kinase inhibitor(s) are administered at different times or simultaneously.
(4) A prophylactic or therapeutic agent for glaucoma or ocular hypertension comprising sepetaprost, which is characterized by being used concomitantly with a Rho-associated coiled-coil containing protein kinase inhibitor(s).
(5) The prophylactic or therapeutic agent described in the above-mentioned (4), which is administered at different time from or simultaneously with the Rho-associated coiled-coil containing protein kinase inhibitor(s).
(6) The prophylactic or therapeutic agent described in any one of the above-mentioned (1) to (5), wherein the Rho-associated coiled-coil containing protein kinase(s) inhibitor is at least one kind selected from the group consisting of ripasudil, netarsudil and a salt thereof
(7) The prophylactic or therapeutic agent described in any one of the above-mentioned (1) to (6), wherein the Rho-associated coiled-coil containing protein kinase inhibitor(s) is ripasudil monohydrochloride dihydrate.
(8) The prophylactic or therapeutic agent described in any one of the above-mentioned (1) to (6), wherein the Rho-associated coiled-coil containing protein kinase inhibitor(s) is dimesylate or dihydrochloride of netarsudil.
Also, the present invention relates to the following.
(9) An intraocular pressure-lowering agent, which is characterized in that sepetaprost and a Rho-associated coiled-coil containing protein kinase inhibitor(s) are combined.
(10) An intraocular pressure-lowering agent comprising sepetaprost, which is characterized by being used concomitantly with a Rho-associated coiled-coil containing protein kinase inhibitor(s).
Further, the present invention relates to the following.
(11) A prophylactic or therapeutic composition for glaucoma or ocular hypertension comprising sepetaprost, which is characterized by being administered in combination with a Rho-associated coiled-coil containing protein kinase inhibitor(s).
(12) A prophylactic or therapeutic method for glaucoma or ocular hypertension comprising: administering a therapeutically effective amount of sepetaprost and a therapeutically effective amount of a Rho-associated coiled-coil containing protein kinase inhibitor(s) to a subject in need thereof.
(13) Use of a combination of sepetaprost and a Rho-associated coiled-coil containing protein kinase inhibitor(s) for manufacturing a medicament for the prophylaxis or treatment for glaucoma or ocular hypertension.
(14) Use of sepetaprost for manufacturing a medicament for the prophylaxis or treatment for glaucoma or ocular hypertension characterized by being used concomitantly with a Rho-associated coiled-coil containing protein kinase inhibitor(s).
(15) Sepetaprost for use in the prophylaxis or treatment for glaucoma or ocular hypertension, which is characterized by being used concomitantly with a Rho-associated coiled-coil containing protein kinase inhibitor(s).
(16) A combination of sepetaprost and a Rho-associated coiled-coil containing protein kinase inhibitor(s) for use in the prophylaxis or treatment for glaucoma or ocular hypertension.
Moreover, the present invention relates to the following.
(17) A composition for lowering an intraocular pressure comprising sepetaprost, which is characterized by being administered in combination with a Rho-associated coiled-coil containing protein kinase inhibitor(s).
(18) A method for lowering an intraocular pressure comprising: administering a therapeutically effective amount of sepetaprost and a therapeutically effective amount of a Rho-associated coiled-coil containing protein kinase inhibitor(s) to a subject in need thereof.
(19) Use of a combination of sepetaprost and a Rho-associated coiled-coil containing protein kinase inhibitor(s) for manufacturing a medicament for lowering an intraocular pressure.
(20) Use of sepetaprost for manufacturing a medicament for lowering an intraocular pressure characterized by being used concomitantly with a Rho-associated coiled-coil containing protein kinase inhibitor(s).
(21) Sepetaprost for use in lowering an intraocular pressure, which is characterized by being used concomitantly with a Rho-associated coiled-coil containing protein kinase inhibitor(s).
(22) A combination of sepetaprost and a Rho-associated coiled-coil containing protein kinase inhibitor(s) for use in lowering an intraocular pressure.
Incidentally, each constitution of the above-mentioned (1) to (22) can be combined by arbitrary selecting two or more.

Effects of the Invention

By administering sepetaprost and a Rho-associated coiled-coil containing protein kinase inhibitor(s) to an eye in combination, an intraocular pressure lowering action is enhanced. Accordingly, the present invention is useful as a prophylactic or therapeutic agent for glaucoma or ocular hypertension. Further, according to the present invention, sufficient safety as a pharmaceutical product is ensured.

DESCRIPTION OF THE EMBODIMENTS

Figure 1:
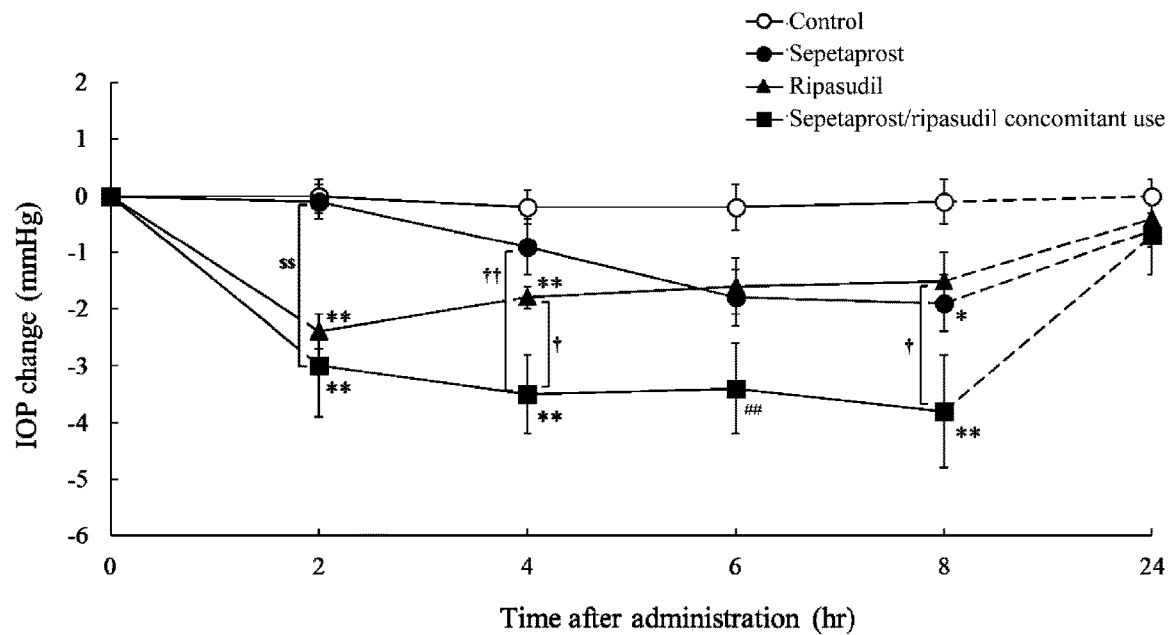
FIG. 1 is a graph showing change in the lowering width of an intraocular pressure with the lapse of time for each administered group of sepetaprost and ripasudil alone, and concomitant use.

In the following, the present invention will be explained in detail.
The present invention is directed to a prophylactic or therapeutic agent for glaucoma or ocular hypertension, which is characterized in that sepetaprost and a Rho-associated coiled-coil containing protein kinase inhibitor(s) are administered in combination, and hereinafter, these are also simply referred to as the "therapeutic agent or the like".

In the therapeutic agent or the like of the present invention, sepetaprost is the compound (CAS registry number: 1262873-06-2) represented by the following formula (1):

[Formula 2]

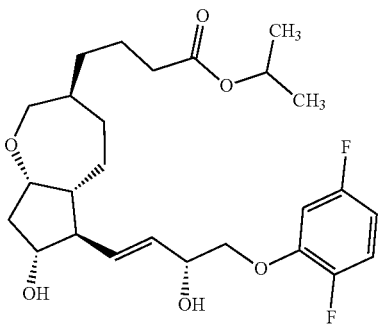

(1)

and is also referred to as 2-propanyl 4-{(3S, 5aR, 6R, 7R, 8aS)-6-[(1E, 3R)-4-(2, 5-difluorophenoxy)-3-hydroxy-1-buten-1-yl]-7-hydroxyoctahydro-2H-cyclopenta[b]oxepin-3-yl}butanoate.

Sepetaprost can be produced in accordance with the methods disclosed in WO 2011/013651 (Patent Document 6), or a usual method in this technical field.

When there are geometric isomers and/or optical isomers in sepetaprost, those isomers are also included in the scope of the present invention.

When there is proton tautomerism in sepetaprost, those tautomers (keto form and enol form) are also included in the scope of the present invention.

When there is crystal polymorphism and/or crystal polymorph group (crystal polymorph system) in sepetaprost, those crystal polymorphs and/or crystal polymorph group (crystal polymorph system) are also included in the scope of the present invention. Here, the crystal polymorph group (crystal polymorph system) means a crystal form at each stage when the crystal form changes to various crystal forms depending on the conditions and/or states (incidentally, in this state, a formulated state is also included) of production, crystallization and preservation of these crystals, and/or the whole thereof.

Sepetaprost may take a form of a hydrate or a solvate.

In the therapeutic agent or the like of the present invention, a content of sepetaprost is not particularly limited, which may vary depending on the administration form, and in the case of eye drops, a lower limit of the content of sepetaprost is preferably 0.000001 to 5% (w/v), and more preferably 0.00001 to 0.05% (w/v). Here, "% (w/v)" means a mass (g) of an active ingredient(s) or an additive(s) contained in 100 mL of the drug. For example, 0.01% (w/v) sepetaprost means that the content of sepetaprost contained in 100 mL of the drug is 0.01 g.

Incidentally, when sepetaprost is in the form of a hydrate or a solvate, the content of sepetaprost may be calculated based on any of a free form, a hydrate or a solvate of sepetaprost.

The Rho-associated coiled-coil containing protein kinase inhibitor(s) in the therapeutic agent or the like of the present invention means a compound which inhibits a serine/threonine kinase activated accompanied by activation of Rho. For example, there may be mentioned ROKα (ROCK-II), p160ROCK (ROKβ, ROCK-I) and other compounds which inhibit a protein having a serine/threonine kinase activity.

As specific examples of the Rho-associated coiled-coil containing protein kinase inhibitor(s), a Rho-associated coiled-coil containing protein kinase inhibitor such as (R)-trans-N-(pyridin-4-yl)-4-(1-aminoethyl)cyclohexanecarboxamide, (R)—(+)—N-(1H-pyrrolo[2, 3-b]pyridin-4-yl)-4-(1-aminoethyl)benzamide or the like disclosed in WO 98/06433 and WO 00/09162; a Rho-associated coiled-coil containing protein kinase inhibitor such as 1-(5-isoquinolinesulfonyl)homopiperazine, 1-(5-isoquinolinesulfonyl)-2-methylpiperazine or the like disclosed in WO 97/23222 and Nature, 389, 990-994 (1997); a Rho-associated coiled-coil containing protein kinase inhibitor such as (1-benzylpyrrolidin-3-yl)-(1H-indazol-5-yl)amine or the like disclosed in WO 01/56988; a Rho-associated coiled-coil containing protein kinase inhibitor such as (1-benzylpiperidin-4-yl)-(1H-indazol-5-yl)amine or the like disclosed in WO 02/100833; a Rho-associated coiled-coil containing protein kinase inhibitor such as N-[2-(4-fluorophenyl)-6,7-dimethoxy-4-quinazolinyl]-N-(1H-indazol-5-yl)amine or the like disclosed in WO 02/076976; a Rho-associated coiled-coil containing protein kinase inhibitor such as N-4-(1H-indazol-5-yl)-6,7-dimethoxy-N-2-pyridin-4-yl-quinazoline-2,4-diamine or the like disclosed in WO 02/076977; a Rho-associated coiled-coil containing protein kinase inhibitor such as 4-methyl-5-(2-methyl-[1,4]diazepane-1-sulfonyl)isoquinoline or the like disclosed in WO 99/64011; a Rho-associated coiled-coil containing protein kinase inhibitor such as (S)-(–)-1-(4-fluoro-5-isoquinolinesulfonyl)-2-methyl-1,4-homopiperazine or the like disclosed in WO 2006/068208; and a Rho-associated coiled-coil containing protein kinase inhibitor such as 4-(3-amino-1-(isoquinolin-6-ylamino)-1-oxopropan-2-yl)benzyl 2,4-dimethylbenzoate or the like disclosed in WO 2010/126626 are exemplified. Among these, in particular, (S)-(–)-1-(4-fluoro-5-isoquinolinesulfonyl)-2-methyl-1,4-homopiperazine, 4-(3-amino-1-(isoquinolin-6-ylamino)-1-oxopropan-2-yl)benzyl 2,4-dimethylbenzoate and [4-[(1S)-1-(aminomethyl)-2-(isoquinolin-6-ylamino)-2-oxoethyl]phenyl]methyl 2,4-dimethylbenzoate are preferred.

In the therapeutic agent or the like of the present invention, a content of the Rho-associated coiled-coil containing protein kinase inhibitor(s) is not particularly limited, which may vary depending on the administration form, and in the case of eye drops, a content of the Rho-associated coiled-coil containing protein kinase inhibitor(s) is preferably 0.0001 to 5% (w/v), and more preferably 0.001 to 1% (w/v).

Incidentally, when the Rho-associated coiled-coil containing protein kinase inhibitor(s) is in the form of a salt, a hydrate or a solvate, the contents of these Rho-associated coiled-coil containing protein kinase inhibitor(s) may be calculated based on any of a free form, a salt, a hydrate or a solvate of the Rho-associated coiled-coil containing protein kinase inhibitor(s).

In the therapeutic agent or the like of the present invention, ripasudil is the compound (CAS registry number: 223645-67-8) represented by the following formula (2)

[Formula 3]

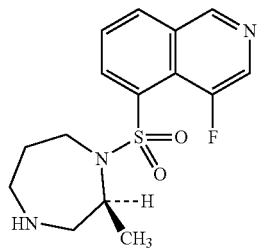

(2)

which is also referred to as (S)-(-)-1-(4-fluoro-5-isoquinolinesulfonyl)-2-methyl-1, 4-homopiperazine. Since it has a Rho-associated coiled-coil containing protein kinase inhibitory action, and promotes drainage of aqueous humor from the main outflow passage via travecula-Schlemm's canal, it has been sold as a therapeutic agent for glaucoma and ocular hypertension (Glanatec (Registered Trademark) eye drops 0.4%).

In the therapeutic agent or the like of the present invention, the salt of ripasudil is not particularly limited as long as it is a pharmacologically acceptable salt. Specific examples include an inorganic acid salt such as hydrochloride, hydrobromide, hydroiodide, nitrate, sulfate or phosphate; an organic acid salt such as acetate, trifluoroacetate, benzoate, oxalate, malonate, succinate, maleate, fumarate, tartrate, citrate, methanesulfonate, ethanesulfonate, trifluoromethanesulfonate, benzenesulfonate, p-toluenesulfonate, glutamate or aspartate; a metal salt such as sodium salt, potassium salt, calcium salt or magnesium salt; an inorganic salt such as ammonium salt; or an organic amine salt such as triethylamine salt or guanidine salt, preferably hydrochloride, and further preferably monohydrochloride.

When there are geometric isomers and/or optical isomers in ripasudil or a salt thereof, those isomers are also included in the scope of the present invention.

When there is proton tautomerism in ripasudil or a salt thereof, those tautomers (keto form and enol form) are also included in the scope of the present invention.

When there is crystal polymorphism and/or crystal polymorph group (crystal polymorph system) in ripasudil or a salt thereof, those crystal polymorphs and/or crystal polymorph group (crystal polymorph system) are also included in the scope of the present invention. Here, the crystal polymorph group (crystal polymorph system) means a crystal form at each stage when the crystal form changes to various crystal forms depending on the conditions and/or states (incidentally, in this state, a formulated state is also included) of production, crystallization and preservation of these crystals, and/or the whole thereof.

In the therapeutic agent or the like of the present invention, ripasudil or a salt thereof may take a form of a hydrate or a solvate. As the salt and hydrate of ripasudil, ripasudil monohydrochloride dihydrate (CAS registry number; 887375-67-9) is most preferable. In the therapeutic agent or the like of the present invention, ripasudil or a salt thereof, or a hydrate or a solvate thereof is also simply referred to as "ripasudil".

In the therapeutic agent or the like of the present invention, a content of ripasudil or a salt thereof is not particularly limited, which may vary depending on the administration form, and in the case of eye drops, a lower limit of the content of ripasudil or a salt thereof is preferably 0.01% (w/v), more preferably 0.05% (w/v), further preferably 0.1% (w/v), and particularly preferably 0.2% (w/v). Also, an upper limit of the above-mentioned content is preferably 3% (w/v), more preferably 2% (w/v), further preferably 1% (w/v), and particularly preferably 0.6% (w/v). In more detail, the above-mentioned content may be a range in which any of the above-mentioned lower limit and upper limit are combined, and preferably 0.01 to 3% (w/v), more preferably 0.05 to 2% (w/v), further preferably 0.1 to 1% (w/v), particularly preferably 0.2 to 0.6% (w/v), and most preferably 0.4% (w/v).

Incidentally, when ripasudil or a salt thereof is in the form of a salt, the contents of these ripasudil or a salt thereof may be calculated based on any of a free form, a salt, a hydrate or a solvate of ripasudil or a salt thereof.

In the therapeutic agent or the like of the present invention, netarsudil is the compound (CAS registry number: 1254032-66-0) represented by the following formula (3):

[Formula 4]

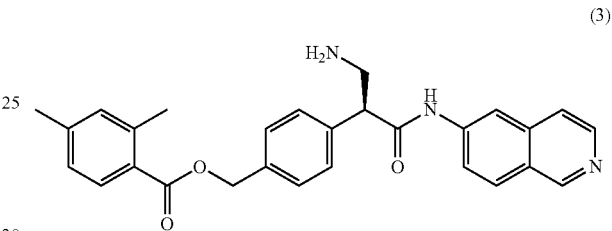

(3)

which is also referred to as [4-[(1S)-1-(aminomethyl)-2-(isoquinolin-6-ylamino)-2-oxoethyl]phenyl]methyl 2,4-dimethylbenzoate. Since it has a Rho-associated coiled-coil containing protein kinase inhibitory action and a norepinephrine transporter (NEP) inhibitory action, and exhibits an intraocular pressure lowering action, it has been sold as a therapeutic agent for glaucoma and ocular hypertension in the United States (RHOPRESSA (Registered Trademark) 0.02%).

In the therapeutic agent or the like of the present invention, the salt of netarsudil is not particularly limited as long as it is a pharmacologically acceptable salt. Specific examples include an inorganic acid salt such as hydrochloride, hydrobromide, hydroiodide, nitrate, sulfate or phosphate; an organic acid salt such as acetate, trifluoroacetate, benzoate, oxalate, malonate, succinate, maleate, fumarate, tartrate, citrate, mesylate (methanesulfonate), ethanesulfonate, trifluoromethanesulfonate, benzenesulfonate, p-toluenesulfonate, glutamate or aspartate; a metal salt such as sodium salt, potassium salt, calcium salt or magnesium salt; an inorganic salt such as ammonium salt; or an organic amine salt such as triethylamine salt or guanidine salt, preferably mesylate (methanesulfonate) or hydrochloride, and more preferably dimesylate (dimethanesulfonate) or dihydrochloride.

When there are geometric isomers and/or optical isomers in netarsudil or a salt thereof, those isomers are also included in the scope of the present invention.

When there is proton tautomerism in netarsudil or a salt thereof, those tautomers (keto form and enol form) are also included in the scope of the present invention.

When there is crystal polymorphism and/or crystal polymorph group (crystal polymorph system) in netarsudil or a salt thereof, those crystal polymorphs and/or crystal polymorph group (crystal polymorph system) are also included in the scope of the present invention. Here, the crystal polymorph group (crystal polymorph system) means a crystal form at each stage when the crystal form changes to various crystal forms depending on the conditions and/or states (incidentally, in this state, a formulated state is also included) of production, crystallization and preservation of these crystals, and/or the whole thereof.

In the therapeutic agent or the like of the present invention, netarsudil or a salt thereof may take a form of a hydrate or a solvate. As the salt and hydrate of netarsudil, netarsudil dimesylate (CAS registry number: 1422144-42-0) is most preferable. In the therapeutic agent or the like of the present invention, netarsudil or a salt thereof, or a hydrate or a solvate thereof is also simply referred to as "netarsudil".

In the therapeutic agent or the like of the present invention, a content of netarsudil or a salt thereof is not particularly limited, which may vary depending on the administration form, and in the case of eye drops, a lower limit of the content of netarsudil or a salt thereof is preferably 0.001% (w/v), more preferably 0.003% (w/v), further preferably 0.005% (w/v), and particularly preferably 0.01% (w/v). Also, an upper limit of the above-mentioned content is preferably 0.2% (w/v), more preferably 0.1% (w/v), further preferably 0.06% (w/v), and particularly preferably 0.04% (w/v). In more detail, the above-mentioned content may be a range in which any of the above-mentioned lower limit and upper limit are combined, and preferably 0.001 to 0.2% (w/v), more preferably 0.003 to 0.1% (w/v), further preferably 0.005 to 0.06% (w/v), particularly preferably 0.01 to 0.04% (w/v), and most preferably 0.02% (w/v).

Incidentally, when netarsudil or a salt thereof is in the form of a salt, a hydrate or a solvate, the contents of these netarsudil or a salt thereof may be calculated based on any of a free form, a salt, a hydrate or a solvate of netarsudil or a salt thereof.

In the therapeutic agent or the like of the present invention, in addition to sepetaprost and the Rho-associated coiled-coil containing protein kinase inhibitor(s), one or more of the other prophylactic or therapeutic agent(s) for glaucoma or ocular hypertension may be further used in combination. The other prophylactic or therapeutic agent(s) for glaucoma or ocular hypertension may be any drug as long as it has an intraocular pressure lowering action and is useful for the treatment for glaucoma, and there may be mentioned non-selective sympathomimetics, $\alpha_2$ receptor agonists, $\alpha_1$ receptor blockers, $\beta$ receptor blockers, parasympathomimetics, carbonic anhydrase inhibitors, prostaglandins and the like.

Specific examples of the non-selective sympathomimetics include dipivefrin, specific examples of the $\alpha_2$ receptor agonists include brimonidine and apraclonidine, specific examples of the $\alpha_1$ receptor blockers include bunazosin, specific examples of the $\beta$ receptor blockers include timolol, befunolol, carteolol, nipradilol, betaxolol, levobunolol and metipranolol, specific examples of the parasympathomimetics include pilocarpine, specific examples of the carbonic anhydrase inhibitors include dorzolamide, brinzolamide and acetazolamide, and specific examples of the prostaglandins include isopropyl unoprostone, latanoprost, travoprost and bimatoprost. These include a form of a salt pharmaceutically acceptable as a medicine. Specific examples of the salt include an inorganic acid salt such as hydrochloride, hydrobromide, hydroiodide, nitrate, sulfate or phosphate; an organic acid salt such as acetate, trifluoroacetate, benzoate, oxalate, malonate, succinate, maleate, fumarate, tartrate, citrate, methanesulfonate, ethanesulfonate, trifluoromethanesulfonate, benzenesulfonate, p-toluenesulfonate, glutamate or aspartate; a metal salt such as sodium salt, potassium salt, calcium salt or magnesium salt; an inorganic salt such as ammonium salt; or an organic amine salt such as triethylamine salt or guanidine salt.

Further, the other prophylactic or therapeutic agent(s) for glaucoma or ocular hypertension may take a form of a hydrate or a solvate.

In the therapeutic agent or the like of the present invention, when it is used in combination with the other prophylactic or therapeutic agent(s) for glaucoma or ocular hypertension, a content thereof is not particularly limited, which may vary depending on a kind and an administration form of the prophylactic or therapeutic agent to be contained, and a preferred content in the case of eye drops is as follows.

The content of the non-selective sympathomimetics may vary depending on a kind of the drug, and in the case of dipivefrin, it is preferably 0.001 to 3% (w/v), more preferably 0.04 to 0.1% (w/v), and particularly preferably 0.04% (w/v) or 0.1% (w/v).

The content of the $\alpha_2$ receptor agonists may vary depending on a kind of the drug, and in the case of brimonidine, it is preferably 0.01 to 5% (w/v), more preferably 0.1 to 0.5% (w/v), and particularly preferably 0.1% (w/v), 0.15% (w/v), 0.2% (w/v) or 0.5% (w/v). Also, in the case of apraclonidine, it is preferably 0.01 to 5% (w/v), more preferably 0.5 to 1% (w/v), and particularly preferably 0.5% (w/v).

The content of the $\alpha_1$ receptor blockers may vary depending on a kind of the drug, and in the case of bunazosin, it is preferably 0.001 to 0.3% (w/v), more preferably 0.003 to 0.03% (w/v), and particularly preferably 0.01% (w/v).

The content of the $\beta$ receptor blockers may vary depending on a kind of the drug, and in the case of timolol, it is preferably 0.01 to 5% (w/v), more preferably 0.1 to 0.5% (w/v), and particularly preferably 0.1% (w/v), 0.25% (w/v) or 0.5% (w/v). Also, in the case of befunolol, it is preferably 0.01 to 5% (w/v), more preferably 0.25 to 1% (w/v), and particularly preferably 0.25% (w/v), 0.5% (w/v) or 1% (w/v). In the case of carteolol, it is preferably 0.01 to 5% (w/v), more preferably 1 to 2% (w/v), and particularly preferably 1% (w/v) or 2% (w/v). In the case of nipradilol, it is preferably 0.01 to 5% (w/v), and particularly preferably 0.25% (w/v). In the case of betaxolol, it is preferably 0.01 to 5% (w/v), more preferably 0.25 to 0.5% (w/v), and particularly preferably 0.25% (w/v) or 0.5% (w/v). In the case of levobunolol, it is preferably 0.01 to 5% (w/v), more preferably 0.25 to 0.5% (w/v), and particularly preferably 0.25% (w/v) or 0.5% (w/v). In the case of metipranolol, it is preferably 0.01 to 5% (w/v), and particularly preferably 0.3% (w/v).

The content of the parasympathomimetics may vary depending on a kind of the drug, and in the case of pilocarpine, it is preferably 0.01 to 20% (w/v), more preferably 0.1 to 5% (w/v), and particularly preferably 0.5% (w/v), 1% (w/v), 2% (w/v), 3% (w/v) or 4% (w/v).

The content of the carbonic anhydrase inhibitors may vary depending on a kind of the drug, and in the case of dorzolamide, it is preferably 0.01 to 5% (w/v), more preferably 0.5 to 2% (w/v), and particularly preferably 0.5% (w/v), 1% (w/v) or 2% (w/v). Also, in the case of brinzolamide, it is preferably 0.01 to 5% (w/v), more preferably 0.1 to 2% (w/v), and particularly preferably 1% (w/v). Also, in the case of acetazolamide, it is preferably 0.01 to 5% (w/v), and more preferably 1 to 5% (w/v). Incidentally, when acetazolamide is orally administered, 250 to 1000 mg may be used as a daily dose.

The content of the prostaglandins may vary depending on a kind of the drug, and in the case of latanoprost, it is preferably 0.0001 to 5% (w/v), more preferably 0.0005 to 1% (w/v), further preferably 0.001 to 0.1% (w/v), and particularly preferably 0.005% (w/v). In the case of isopropyl unoprostone, it is preferably 0.001 to 5% (w/v), more preferably 0.01 to 1% (w/v), further preferably 0.12 to 0.15% (w/v), and particularly preferably 0.12% (w/v) or 0.15% (w/v). In the case of bimatoprost, it is preferably 0.0001 to 5% (w/v), more preferably 0.001 to 1% (w/v), further preferably 0.01 to 0.03% (w/v), and particularly preferably 0.01% (w/v) or 0.03% (w/v). In the case of travoprost, it is preferably 0.0001 to 5% (w/v), more preferably 0.001 to 1% (w/v), and particularly preferably 0.004% (w/v).

Incidentally, when the other prophylactic or therapeutic agent(s) for glaucoma or ocular hypertension is in the form of a salt, a hydrate or a solvate, the content of the other prophylactic or therapeutic agent(s) for glaucoma or ocular hypertension may be calculated based on any of a free form, a salt, a hydrate or a solvate of the other prophylactic or therapeutic agent(s) for glaucoma or ocular hypertension.

In the therapeutic agent or the like of the present invention, in place of the Rho-associated coiled-coil containing protein kinase inhibitor(s), one or more of the other prophylactic or therapeutic agent(s) for glaucoma or ocular hypertension may be used in combination with sepetaprost. As the other prophylactic or therapeutic agent(s) for glaucoma or ocular hypertension, any substance may be used, as long as it has an intraocular pressure lowering action or a neuroprotective action and is useful for the treatment for glaucoma, there may be mentioned non-selective sympathomimetics, $\alpha_2$ receptor agonists, al receptor blockers, parasympathomimetics, carbonic anhydrase inhibitors, prostaglandins, NMDA antagonists, and the like, and specific examples thereof or contents thereof are as described above. As examples of more specific combination, there may be mentioned a combination of sepetaprost and dipivefrin, a combination of sepetaprost and brimonidine, a combination of sepetaprost and apraclonidine, a combination of sepetaprost and bunazosin, a combination of sepetaprost and pilocarpine, a combination of sepetaprost and carbachol, a combination of sepetaprost and demecarium, a combination of sepetaprost and echothiphate, a combination of sepetaprost and distigmine bromide, a combination of sepetaprost and dorzolamide, a combination of sepetaprost and brinzolamide, a combination of sepetaprost and acetazolamide, a combination of sepetaprost and diclofenamide, a combination of sepetaprost and methazolamide, a combination of sepetaprost and isopropyl unoprostone, a combination of sepetaprost and latanoprost, a combination of sepetaprost and travoprost, and a combination of sepetaprost and bimatoprost.

The therapeutic agent or the like of the present invention is characterized in that sepetaprost and the Rho-associated coiled-coil containing protein kinase inhibitor(s) are administered in combination whereby glaucoma or ocular hypertension is to be prevented or treated. As the glaucoma in the therapeutic agent or the like of the present invention, primary open-angle glaucoma, secondary open-angle glaucoma, normal tension glaucoma, hypersecretion glaucoma, primary angle-closure glaucoma, secondary angle-closure glaucoma, plateau iris glaucoma, combined-mechanism glaucoma, developmental glaucoma, steroid induced glaucoma, exfoliation glaucoma, amyloid glaucoma, neovascular glaucoma, malignant glaucoma, capsular glaucoma of the lens, plateau iris syndrome and the like are exemplified.

In the therapeutic agent or the like of the present invention, as for the dosage form, a formulation comprising sepetaprost, and a separate formulation comprising the Rho-associated coiled-coil containing protein kinase inhibitor(s) may be administered (concomitant administration), or a single formulation (combination drug) comprising sepetaprost and the Rho-associated coiled-coil containing protein kinase inhibitor(s) may be administered. Also, when one or more of the other prophylactic or therapeutic agent(s) for glaucoma or ocular hypertension is used in combination in addition to sepetaprost and the Rho-associated coiled-coil containing protein kinase inhibitor(s), then, sepetaprost and the Rho-associated coiled-coil containing protein kinase inhibitor(s), and the other prophylactic or therapeutic agent(s) for glaucoma or ocular hypertension may be administered concomitantly, a combination drug comprising optional component(s) of these and the remaining component(s) may be administered concomitantly, or a combination drug comprising all the components may be administered.

The therapeutic agent or the like of the present invention may be administered orally or parenterally, no particular technique is required for formulation thereof, and a formulation can be prepared by using a commonly used technique. As dosage forms, there may be mentioned eye drops, eye ointments, injections, tablets, capsules, granules, powders and the like, and eye drops or eye ointments are preferred.

When sepetaprost and the Rho-associated coiled-coil containing protein kinase inhibitor(s), and the other prophylactic or therapeutic agent(s) for glaucoma or ocular hypertension are separately formulated, formulations can be each prepared according to the known method. As a formulation of the Rho-associated coiled-coil containing protein kinase inhibitor(s) or the other prophylactic or therapeutic agent for glaucoma or ocular hypertension, formulations already commercially available such as ripasudil, netarsudil, dipivefrin, brimonidine, apraclonidine, bunazosin, timolol, befunolol, carteolol, nipradilol, betaxolol, levobunolol, metipranolol, pilocarpine, dorzolamide, brinzolamide, acetazolamide, isopropyl unoprostone, latanoprost, travoprost, bimatoprost, Cosopt (Registered Trademark) combination eye drops, Xalacom (Registered Trademark) combination eye drops, DuoTrav (Registered Trademark) combination eye drops and the like or a substance(s) corresponding to these may be also used.

Also, when one formulation containing the respective components is to be prepared, it can be prepared according to a known method.

In the case of preparing eye drops, sepetaprost and the Rho-associated coiled-coil containing protein kinase inhibitor(s) are added to purified water, a buffer solution or the like, and stirred, and then, a pH of the mixture is adjusted with a pH adjusting agent to prepare a desired eye drop. In addition, if necessary, an additive(s) commonly used in eye drops may be used, and as the additives, there may be mentioned an isotonic agent, a buffering agent, a surfactant, a stabilizer, a preservative, a solubilizing agent, and the like.

A pH of the eye drops may be within the range which is allowable for ophthalmic formulations, it is preferably in the range of pH 4 to 8, and more preferably in the range of pH 5 to 7.

In the case of preparing eye ointments, it can be prepared by using a commonly used base, and as the base, there may be mentioned white petrolatum, liquid paraffin, and the like.

In the case of preparing oral formulations such as tablets, capsules, granules, powders, and the like, it can be prepared by adding a bulking agent, a lubricant, a binder, a disintegrating agent, a coating agent, a film agent, and the like, as necessary. As the bulking agent, there may be mentioned lactose, crystalline cellulose, starch, vegetable oil, and the like, as the lubricant, there may be mentioned magnesium stearate, talc, and the like, as the binder, there may be mentioned hydroxypropyl cellulose, polyvinylpyrrolidone, and the like, as the disintegrating agent, there may be mentioned carboxymethylcellulose calcium, low-substituted hydroxypropylmethyl cellulose, and the like, as the coating agent, there may be mentioned hydroxypropyl methylcellulose, macrogol, silicone resin, and the like, and as the film agent, there may be mentioned a gelatin film, and the like.

An administration method of the therapeutic agent or the like of the present invention can be appropriately changed depending on the dosage form, the severity of symptoms of a patient to be administered to, the age, the body weight, the administration route, the judgment of a doctor, and the like, and in the case of a combination drug comprising sepetaprost and a Rho-associated coiled-coil containing protein kinase inhibitor(s), it may be administered 1 to 5 times a day, preferably once or twice a day, and most preferably once a day. When a formulation comprising sepetaprost and a formulation comprising a Rho-associated coiled-coil containing protein kinase inhibitor(s) are administered concomitantly, each formulation may be administered at different times or simultaneously 1 to 3 times a day, preferably once or twice a day, and most preferably once a day. Incidentally, in the concomitant administration, when the formulations are administered at different times, the order of administering the formulations is not limited, and after one formulation is administered, the other formulation may be administered within 12 hours, preferably within 6 hours, more preferably within 1 hour, further preferably within 30 minutes, particularly preferably within 5 minutes, and most preferably promptly. In the above-mentioned administration method, in the case of eye drop administration, it is preferable to administer 1 to 3 drops per once, more preferably to administer 1 or 2 drops, and most preferably to administer 1 drop.

The detailed description of the above-mentioned therapeutic agent or the like of the present invention is also applied to the prophylactic or therapeutic agent for glaucoma or ocular hypertension comprising sepetaprost of the present invention, which is characterized by being used concomitantly with a Rho-associated coiled-coil containing protein kinase inhibitor(s). The detailed description of the above-mentioned therapeutic agent or the like of the present invention is also applied to an intraocular pressure-lowering agent of the present invention, which is characterized in that sepetaprost and a Rho-associated coiled-coil containing protein kinase inhibitor(s) are combined. The detailed description of the above-mentioned therapeutic agent or the like of the present invention is also applied to an intraocular pressure-lowering agent of the present invention comprising sepetaprost, which is characterized by being used concomitantly with a Rho-associated coiled-coil containing protein kinase inhibitor(s).

Also, detailed description of the above-mentioned therapeutic agent or the like of the present invention is also applied to the embodiment of the present invention mentioned below.

One embodiment of the present invention is a composition for the prophylaxis or treatment for glaucoma or ocular hypertension comprising sepetaprost, which is characterized by being administered in combination with a Rho-associated coiled-coil containing protein kinase inhibitor(s).

One embodiment of the present invention is a prophylactic or therapeutic method for glaucoma or ocular hypertension comprising: administering a therapeutically effective amount of sepetaprost, and a therapeutically effective amount of a Rho-associated coiled-coil containing protein kinase inhibitor(s) in combination to a subject in need thereof.

One embodiment of the present invention is use of a combination of sepetaprost and a Rho-associated coiled-coil containing protein kinase inhibitor(s) for manufacturing a medicament for the prophylaxis or treatment for glaucoma or ocular hypertension One embodiment of the present invention is use of sepetaprost for manufacturing a medicament for the prophylaxis or treatment for glaucoma or ocular hypertension, which characterized by being used concomitantly with a Rho-associated coiled-coil containing protein kinase inhibitor(s).

One embodiment of the present invention is sepetaprost for use in the prophylaxis or treatment for glaucoma or ocular hypertension, which is characterized by being used concomitantly with a Rho-associated coiled-coil containing protein kinase inhibitor(s).

One embodiment of the present invention is a combination of sepetaprost and a Rho-associated coiled-coil containing protein kinase inhibitor(s) for use in the prophylaxis or treatment for glaucoma or ocular hypertension.

One embodiment of the present invention is a composition for lowering an intraocular pressure comprising sepetaprost, which is characterized by being administered in combination with a Rho-associated coiled-coil containing protein kinase inhibitor(s).

One embodiment of the present invention is a method for lowering an intraocular pressure comprising: administering a therapeutically effective amount of sepetaprost, and a therapeutically effective amount of a Rho-associated coiled-coil containing protein kinase inhibitor(s) to a subject in need thereof.

One embodiment of the present invention is use of a combination of sepetaprost and a Rho-associated coiled-coil containing protein kinase inhibitor(s) for manufacturing a medicament for lowering an intraocular pressure.

One embodiment of the present invention is use of sepetaprost for manufacturing a medicament for lowering an intraocular pressure characterized by being used concomitantly with a Rho-associated coiled-coil containing protein kinase inhibitor(s).

One embodiment of the present invention is sepetaprost for use in lowering an intraocular pressure, which is characterized by being used concomitantly with a Rho-associated coiled-coil containing protein kinase inhibitor(s).

One embodiment of the present invention is a combination of sepetaprost and a Rho-associated coiled-coil containing protein kinase inhibitor(s) for use in lowering an intraocular pressure.

EXAMPLES

In the following, results of pharmacological tests are shown, but these are for better understanding of the present invention and do not limit the scope of the present invention.
[Pharmacological Test]

Example 1

In order to examine usefulness of the combination of sepetaprost and a Rho-associated coiled-coil containing protein kinase inhibitor(s), the effect of lowering an intraocular pressure when sepetaprost and ripasudil which is a Rho-associated coiled-coil containing protein kinase inhibitor were administered concomitantly to experimental animals (normal pressure monkeys) was investigated.
(Preparation of Compound Solutions to be Tested)
(1) Preparation of Sepetaprost Solution
Sepetaprost was dissolved in purified water containing a solubilizing agent, and then, a sepetaprost solution with a desired concentration was prepared by using a commonly used method.
(2) Preparation of Ripasudil Solution
Commercially available ripasudil eye drop (Kowa Company, Ltd., GLANATEC (Registered Trademark) eye drops 0.4%) was used as it was.
(Test Method)
An effect of lowering an intraocular pressure when sepetaprost and ripasudil were administered concomitantly was investigated. As a comparative subject, an effect of lowering an intraocular pressure when sepetaprost or ripasudil was administered alone was also investigated. As a control, the base of the sepetaprost solution and physiological saline solution were administered.
(Drugs and Animals Used in the Test)
  *Sepetaprost* solution: 0.0003% (w/v) sepetaprost solution (volume of eye dropped: 20 μL/eye)
  Ripasudil solution: 0.4% (w/v) ripasudil solution (trade name: GLANATEC (Registered Trademark) eye drops 0.4%, volume of eye dropped: 20 μL/eye)
  Experimental animal: cynomolgus monkey (sex: male, 8 monkeys per a group)
(Administration Method and Measurement Method)
[1] Concomitant Administration of *Sepetaprost* and Ripasudil
  (1) A drop of 0.4% oxybuprocaine hydrochloride eye drop (trade name: Benoxil (Registered Trademark) eye drops 0.4%) was applied to one eye of an experimental animal and local anesthesia was conducted.
  (2) Immediately before administration of a compound solution to be tested, an intraocular pressure was measured and the value was made an intraocular pressure (0 hour) before administration.
  (3) The sepetaprost solution was applied to one eye of an experimental animal (the contralateral eye was untreated). After a short time (after about 5 minutes), the ripasudil solution was applied to the same eye.
  (4) After 2 hours, 4 hours, 6 hours, 8 hours and 24 hours from applying the sepetaprost solution to the eye, one drop of 0.4% oxybuprocaine hydrochloride eye drop was applied to the eye to be measured for the intraocular pressure respectively, and after local anesthesia, the intraocular pressure was measured. Also, the intraocular pressure was measured each three times, and the average value was calculated. With respect to the changed value of the intraocular pressure (mmHg), a difference from the value of the intraocular pressure before administration at each measurement time point was calculated.
[2] Single Administration of *Sepetaprost*
The test was carried out in the same manner as the above-mentioned concomitant administration test except for changing the ripasudil solution to the physiological saline solution.
[3] Single Administration of Ripasudil
The test was carried out in the same manner as the above-mentioned concomitant administration test except for changing the sepetaprost solution to the base of the sepetaprost solution.

[4] Control
The test was carried out in the same manner as the above-mentioned concomitant administration test except for changing the sepetaprost solution to the base of the sepetaprost solution and changing the ripasudil solution to the physiological saline solution.
(Results)
The changes in the lowering of the intraocular pressure with the lapse of time for each administered group are shown in FIG. 1 and Table 1. The changes in the intraocular pressure values are shown by an average value ±SEM of the difference from the value (0 hour) before administration of eight monkeys in each group with regard to each measurement time point of each individual. Comparison of the control group with the sepetaprost group, the ripasudil group, or the sepetaprost/ripasudil concomitant use group, and comparison of the sepetaprost/ripasudil concomitant use group with the sepetaprost group or the ripasudil group was carried out by, after carrying out the Bartlett test, in the case where dispersion is uniform, using the Dunnett test, or in the case of ununiform, using the Steel test. The significance level with respect to the control group was shown as ##: $p<0.01$ in the Dunnett test, and *: $p<0.05$ and **: $p<0.01$ in the Steel test. The significance level with respect to the sepetaprost/ripasudil concomitant group was shown as†: $p<0.05$ and ††: $p<0.01$ in the Dunnett test, and $$: $p<0.01$ in the Steel test.

TABLE 1

| Time after dropping | 2 | 4 | 6 | 8 | 24 |
|---|---|---|---|---|---|
| Control | 0.0 | −0.2 | −0.2 | −0.1 | 0.0 |
| Sepetaprost | −0.1 | −0.9 | −1.8 | −1.9 | −0.6 |
| Ripasudil | −2.4 | −1.8 | −1.6 | −1.5 | −0.4 |
| Sepetaprost/ ripasudil concomitant use | −3.0 | −3.5 | −3.4 | −3.8 | −0.7 |

As clearly seen from FIG. 1 and Table 1, the concomitantly administered group of sepetaprost and ripasudil showed more excellent intraocular pressure lowering action and sustained effect of the action than the single drug administered group, that is, the sepetaprost administered group and the ripasudil administered group. In particular, at 2, 4 and 8 hours after administration, the amounts of change in the intraocular pressure values for the concomitantly administered group of sepetaprost and ripasudil was larger than the sum of the amounts of change in the intraocular pressure values for the sepetaprost administered group and for the ripasudil administered group, and the synergistic effect of the intraocular pressure lowering action was confirmed.

From the above, it was found that by combining sepetaprost with a Rho-associated coiled-coil containing protein kinase inhibitor(s), more potent intraocular pressure lowering action and a sustained effect of the action can be obtained.

Example 2

In order to examine usefulness of the combination of sepetaprost and a Rho-associated coiled-coil containing protein kinase inhibitor(s), the effect of lowering an intraocular pressure when sepetaprost and netarsudil which is a Rho-associated coiled-coil containing protein kinase inhibitor were administered concomitantly to experimental animals (normal pressure monkeys) was investigated.

(Preparation of Compound Solutions to be Tested)
(1) Preparation of *Sepetaprost* Solution

*Sepetaprost* was dissolved in purified water containing a solubilizing agent, and then, a sepetaprost solution with a desired concentration was prepared by using a commonly used method.

(2) Preparation of Netarsudil Solution

Dimesylate of netarsudil was dissolved in a physiological saline solution containing a solubilizing agent, and then, a netarsudil solution having a desired concentration was prepared by using a commonly used method.

(Test Method)

An effect of lowering an intraocular pressure when sepetaprost and netarsudil were administered concomitantly was investigated. As a comparative subject, an effect of lowering an intraocular pressure when sepetaprost or netarsudil was administered alone was also investigated. As a control, the base of the sepetaprost solution and the base of the netarsudil solution were administered.

(Drugs and Animals Used in the Test)
*Sepetaprost* solution: 0.0003% (w/v) sepetaprost solution (volume of eye dropped: 20 μL/eye)
Netarsudil solution: 0.01% (w/v) netarsudil solution (volume of eye dropped: 20 μL/eye)
Experimental animal: cynomolgus monkey (sex: male, 8 monkeys per a group)

(Administration Method and Measurement Method)
[1] Concomitant Administration of *Sepetaprost* and Netarsudil
(1) A drop of 0.4% oxybuprocaine hydrochloride eye drop (trade name: Benoxil (Registered Trademark) eye drops 0.4%) was applied to one eye of the experimental animal and local anesthesia was conducted.
(2) Immediately before administration of a compound solution to be tested, an intraocular pressure was measured and the value was made an intraocular pressure (0 hour) before administration.
(3) The sepetaprost solution was applied to one eye of the experimental animal (the contralateral eye was untreated). After a short time (after about 5 minutes), the netarsudil solution was applied to the same eye.
(4) After 2 hours, 4 hours, 6 hours, 8 hours and 24 hours from applying the sepetaprost solution to the eye, one drop of 0.4% oxybuprocaine hydrochloride eye drop was applied to the eye to be measured for the intraocular pressure respectively, and after local anesthesia, the intraocular pressure was measured. Also, the intraocular pressure was measured each three times, and the average value was calculated. With respect to the changed value of the intraocular pressure (mmHg), a difference from the value of the intraocular pressure before administration at each measurement time point was calculated.

[2] Single Administration of *Sepetaprost*

The test was carried out in the same manner as the above-mentioned concomitant administration test except for changing the netarsudil solution to the base of the netarsudil solution.

[3] Single Administration of Netarsudil

The test was carried out in the same manner as the above-mentioned concomitant administration test except for changing the sepetaprost solution to the base of the sepetaprost solution.

[4] Control

The test was carried out in the same manner as the above-mentioned concomitant administration test except for changing the sepetaprost solution to the base of the sepetaprost solution and changing the netarsudil solution to the base of the netarsudil solution.

(Results)

Figure 2:
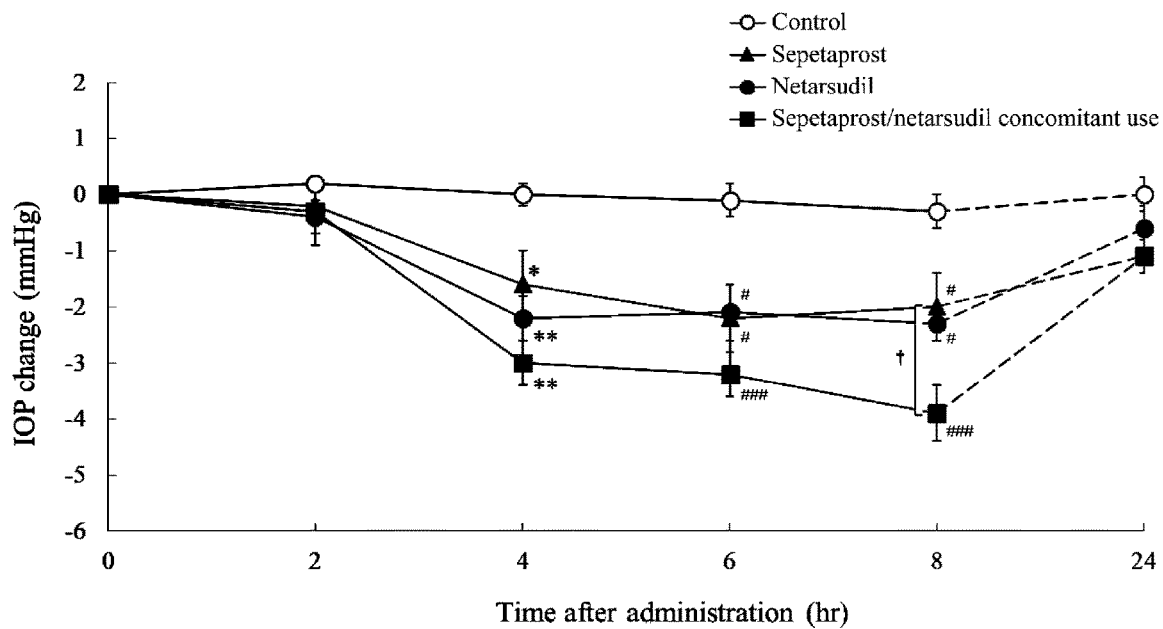
FIG. 2 is a graph showing change in the lowering width of an intraocular pressure with the lapse of time for each administered group of sepetaprost and netarsudil alone, and concomitant use.

The changes in the lowering of the intraocular pressure with the lapse of time for each administered group are shown in FIG. 2 and Table 2. The change in the intraocular pressure values are shown by an average value ±SEM of the difference from the value (0 hour) before administration of eight monkeys in each group with regard to each measurement time point of each individual. Comparison of the control group with the sepetaprost group, the netarsudil group, or the sepetaprost/netarsudil concomitant use group, and comparison of the sepetaprost/netarsudil concomitant use group with the sepetaprost group or the netarsudil group was carried out by, after carrying out the Bartlett test, in the case where dispersion is uniform, using the Dunnett test, or in the case of ununiform, using the Steel test. The significance level with respect to the control group was shown as *: $p<0.05$ and **: $p<0.01$ in the Steel test, and *: #: $p<0.05$ and ###: $p<0.001$ in the Dunnett test. The significance level with respect to the sepetaprost/netarsudil concomitant use group was shown as †: $p<0.05$ in the Dunnett test.

TABLE 2

| Time after dropping | 2 | 4 | 6 | 8 | 24 |
|---|---|---|---|---|---|
| Control | 0.2 | 0.0 | −0.1 | −0.3 | 0.0 |
| Sepetaprost | −0.2 | −1.6 | −2.2 | −2.0 | −1.1 |
| Netarsudil | −0.4 | −2.2 | −2.1 | −2.3 | −0.6 |
| Sepetaprost/ netarsudil concomitant use | −0.3 | −3.0 | −3.2 | −3.9 | −1.1 |

As clearly seen from FIG. 2 and Table 2, the concomitantly administered group of sepetaprost and netarsudil showed more excellent intraocular pressure lowering action and sustained effect of the action than the single drug administered group, that is, the sepetaprost administered group and the netarsudil administered group.

From the above, it was found that by combining sepetaprost with a Rho-associated coiled-coil containing protein kinase inhibitor(s), more potent intraocular pressure lowering action and a sustained effect of the action can be obtained.

INDUSTRIAL APPLICABILITY

When sepetaprost and a Rho-associated coiled-coil containing protein kinase inhibitor(s) are combined and administered to the eye, an intraocular pressure lowering action is enhanced. Therefore, the present invention is useful as a prophylactic or therapeutic agent for glaucoma or ocular hypertension.

The invention claimed is:

1. A therapeutic agent for glaucoma or ocular hypertension, wherein sepetaprost and a Rho-associated coiled-coil containing protein kinase inhibitor(s) are administered in combination, and wherein the Rho-associated coiled-coil containing protein kinase inhibitor(s) is at least one selected from the group consisting of netarsudil and a salt thereof, and wherein sepetaprost and the Rho-associated coiled-coil containing protein kinase inhibitor(s) are administered simultaneously or concomitantly.

2. The therapeutic agent according to claim 1, which is a combination drug comprising sepetaprost and the Rho-associated coiled-coil containing protein kinase inhibitor(s).

3. The therapeutic agent according to claim 1, wherein sepetaprost and the Rho-associated coiled-coil containing protein kinase inhibitor(s) are administered at different times or simultaneously.

4. A therapeutic agent for glaucoma or ocular hypertension comprising sepetaprost, which is used concomitantly with a Rho-associated coiled-coil containing protein kinase inhibitor(s), and wherein the Rho-associated coiled-coil containing protein kinase inhibitor(s) is at least one selected from the group consisting of netarsudil and a salt thereof.

5. The therapeutic agent according to claim 4, which is administered at different time from or simultaneously with the Rho-associated coiled-coil containing protein kinase inhibitor(s).

6. The therapeutic agent according to claim 1, wherein the Rho-associated coiled-coil containing protein kinase inhibitor(s) is dimesylate or dihydrochloride of netarsudil.

7. A therapeutic method for glaucoma or ocular hypertension comprising: administering a therapeutically effective amount of sepetaprost and a therapeutically effective amount of a Rho-associated coiled-coil containing protein kinase inhibitor(s) to a subject in need thereof, and wherein the Rho-associated coiled-coil containing protein kinase inhibitor(s) is at least one selected from the group consisting of netarsudil and a salt thereof, and wherein sepetaprost and the Rho-associated coiled-coil containing protein kinase inhibitor(s) are administered simultaneously or concomitantly.

8. The therapeutic method for glaucoma or ocular hypertension according to claim 7, wherein sepetaprost and the Rho-associated coiled-coil containing protein kinase inhibitor(s) are administered as a combination drug.

9. The therapeutic method for glaucoma or ocular hypertension according to claim 7, wherein sepetaprost and the Rho-associated coiled-coil containing protein kinase inhibitor(s) are administered at different times or simultaneously.

10. The therapeutic method for glaucoma or ocular hypertension according to claim 7, wherein the Rho-associated coiled-coil containing protein kinase inhibitor(s) is dimesylate or dihydrochloride of netarsudil.

11. The therapeutic agent according to claim 4, wherein the Rho-associated coiled-coil containing protein kinase inhibitor(s) is dimesylate or dihydrochloride of netarsudil.

* * * * *